United States Patent [19]
Brooker

[11] 4,306,098
[45] Dec. 15, 1981

[54] NOVEL MANUFACTURE OF 2,4,5-TRICHLOROPHENOL

[75] Inventor: Edgar G. Brooker, New Plymouth, New Zealand

[73] Assignee: Ivon Watkins-Dow Limited, New Plymouth, New Zealand

[21] Appl. No.: 166,202

[22] Filed: Jul. 7, 1980

[51] Int. Cl.³ .................... C07C 37/00; C07C 37/01
[52] U.S. Cl. ................................ 568/776; 568/774
[58] Field of Search ................... 568/716, 774, 776

[56] References Cited
U.S. PATENT DOCUMENTS
2,403,748 7/1946 Olin .

OTHER PUBLICATIONS

Kulka, "J. Amr. Chem. Soc.", vol. 76, Nov. 5, (1954), pp. 5469-5471.
Buehler et al., "Survey of Organic Synthesis", pp. 254, 255 and 258, Wiley-Interscience, N.Y., N.Y., (1970).
Harrison et al., "Compendium of Organic Synthesis Methods", pp. 92-95, Wiley-Interscience, (1971).
Derwent, Week E-10, Section E2C,9F, Japan, (Kokai), No. 50-077,329, (1975).
Esposito et al., "Dioxins", U.S. Environment Protection Agency, Cincinnati, Ohio, EPA-600/2-80-197, Nov. 1980, pp. 5, 6, 78-81, Sect. 2, pp. 3-123.

*Primary Examiner*—Werren B. Lone
*Attorney, Agent, or Firm*—S. Preston Jones; Ronald G. Brookens; John M. Sanders

[57] ABSTRACT

A method of producing 2,4,5-trichlorophenol with low levels of the impurity 2,3,7,8-tetrachlorodibenzo-p-dioxin.

5 Claims, 2 Drawing Figures

NOVEL MANUFACTURE OF 2,4,5-TRICHLOROPHENOL

BACKGROUND OF THE INVENTION 2,4,5-Trichlorophenol is conventionally manufactured by high pressure, high temperature hydrolysis of 1,2,4,5-tetrachlorobenzene using methanolic sodium hydroxide. The overall tetrachlorobenzene hydrolysis is known to proceed via the intermediate 2,4,5-trichloroanisole. Two reactions occur simultaneously, viz. conversion of tetrachlorobenzene to trichloroanisole and demethylation of trichloroanisole to trichlorophenol.

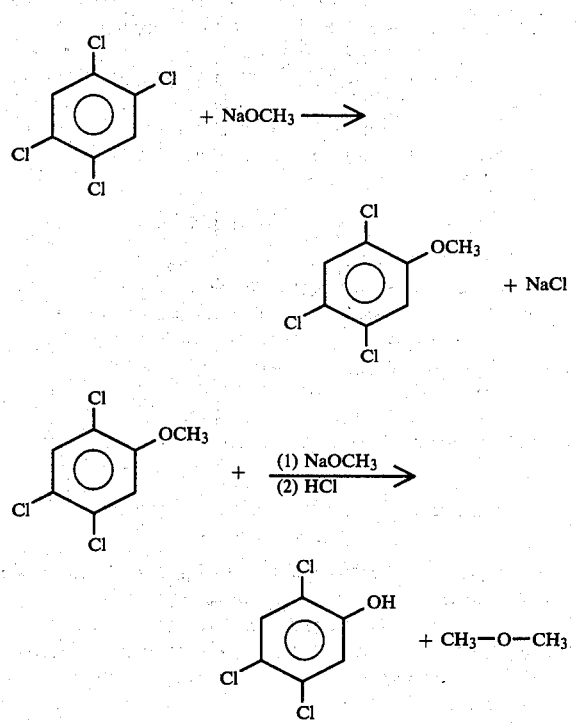

It is also known that the impurity 2,3,7,8-tetrachlorodibenzo-p-dioxin (TCDD) results from the condensation of two molecules of sodium trichlorophenate under conditions of high temperature and high alkalinity.

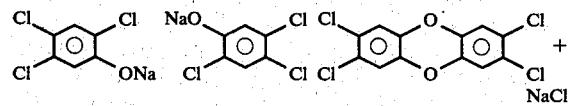

In tetrachlorobenzene hydrolysis, the concentrations of TCDD increase progressively with hydrolysis time. The rate of formation of TCDD is greater towards the end of the hydrolysis, being dependent on sodium trichlorophenate concentration. If the overall hydrolyses are run for progressively shorter periods, reduced concentrations of the desired 2,4,5-trichlorophenol are obtained.

It has now been found that, if the trichloroanisole demethylation is carried out at lower temperatures, under less alkaline or even acidic conditions, and for shorter reaction time periods that TCDD formation can be minimized.

It is known that some substituted anisoles may be demethylated by treatment with Lewis acids, although there are no literature references to the demethylation of chlorinated anisoles by this method.

SUMMARY OF THE INVENTION

This invention relates to a novel process for manufacturing 2,4,5-trichlorophenol containing very low levels (less than 2 parts per billion (ppb)) of the impurity TCDD. TCDD is well known for its extremely high toxicity and other potentially hazardous, biological properties and is an undesirable impurity in 2,4,5-trichlorophenol or its derivatives, which include 2,4,5-trichlorophenoxyacetic acid.

It has now been found that 2,4,5-trichloroanisole can be demethylated to yield high purity 2,4,5-trichlorophenol with very low TCDD content (less than 2 ppb) by heating with aluminium chloride in an organic solvent.

DETAILED DESCRIPTION OF THE INVENTION

Figure 1:
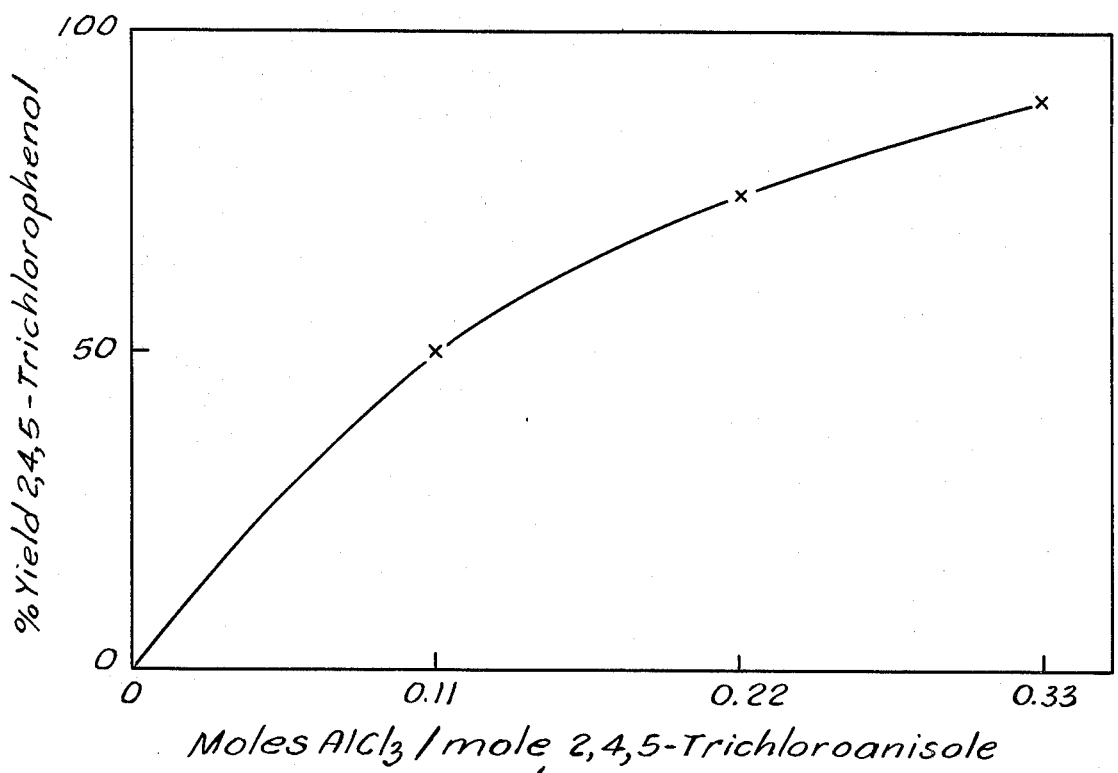
Figure 2:
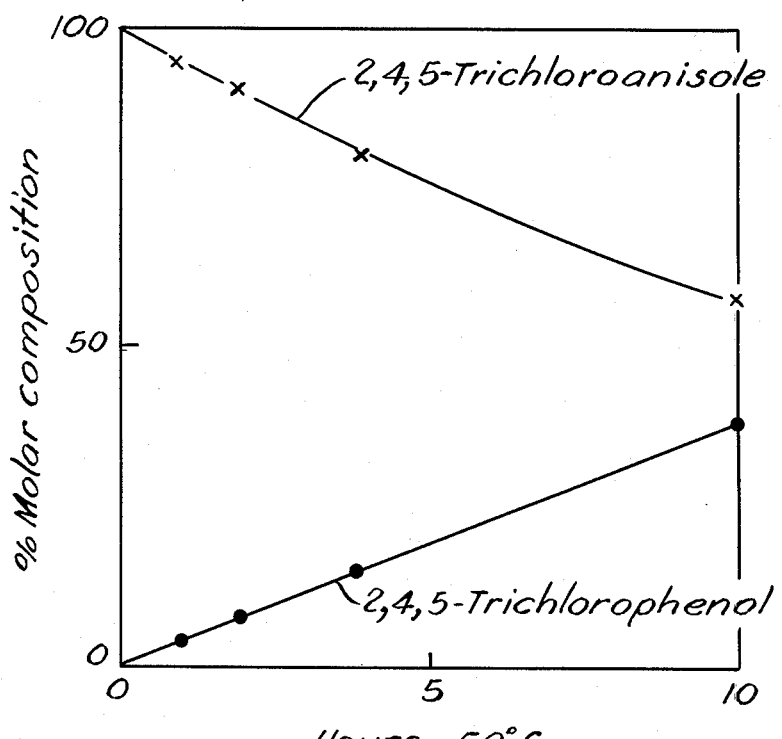
Figure 3:
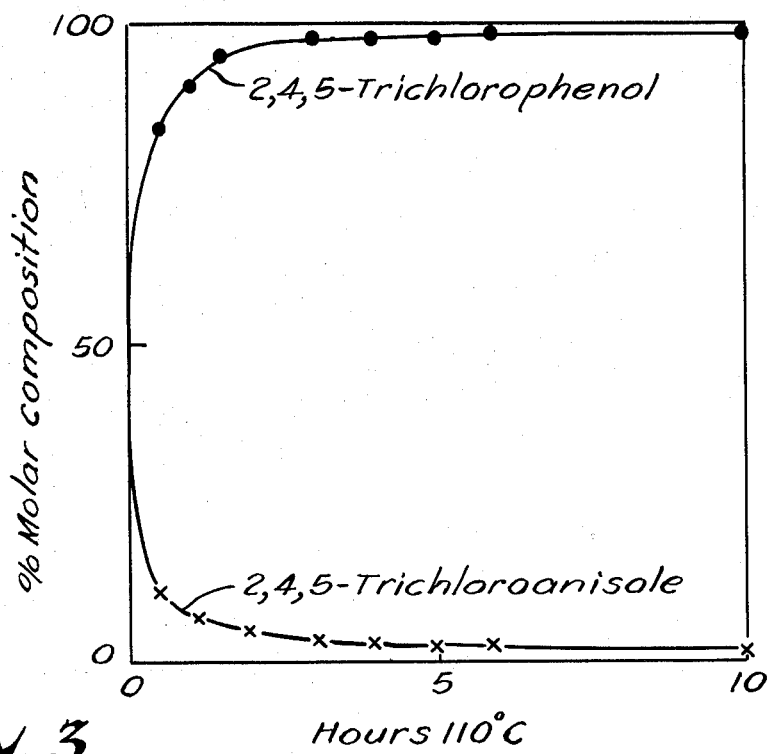
Figure 4:
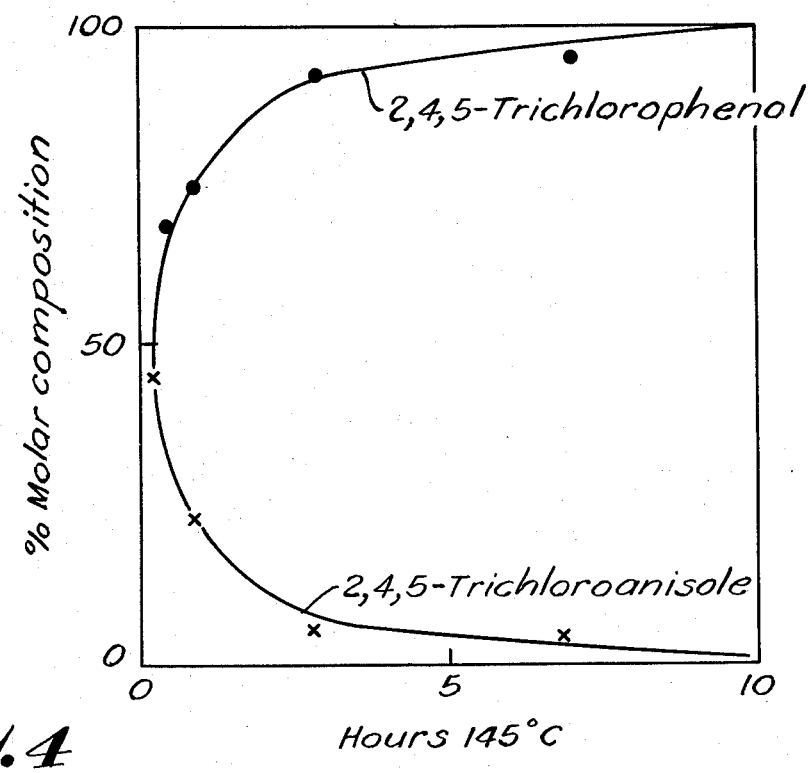

Accordingly, the present invention provides a process for the production of 2,4,5-trichlorophenol containing very low concentrations (less than 2 ppb) of the impurity 2,3,7,8-tetrachlorodibenzo-p-dioxin, (TCDD) which process comprises the demethylation of 2,4,5-trichloroanisole (which may contain minor amounts of the starting 1,2,4,5-tetrachlorobenzene) by treatment with aluminium chloride at temperatures ranging from about 25° C. to the reflux temperature in an aromatic, chloroaromatic, aliphatic or chloroaliphatic hydrocarbon solvent.

As indicated above, the process of the invention may be employed in the treatment of 2,4,5-trichloroanisole which has been prepared by hydrolysis of 1,2,4,5-tetrachlorobenzene and which can contain unhydrolysed tetrachlorobenzene. The tetrachlorobenzene does not interfere with the demethylation reaction and thus remains unchanged during the demethylation reaction.

The process of the invention is preferably carried out in the presence of xylene as the solvent. Other water-immiscible aromatic, chloroaromatic, aliphatic and chloroaliphatic hydrocarbons may be used as the solvent but the yields of trichlorophenol tend to be lower than when xylene is used.

Although aluminium chloride is a member of the class of Lewis acids, other Lewis acids have not been found effective or useful in the process of the invention. Ferric chloride did not effect significant demethylation. Only a 24% yield of 2,4,5-trichlorophenol was obtained when trichloroanisole was treated with a large excess of concentrated sulphuric acid for six hours at 75° C. in the absence of solvent. Other Lewis acids, viz. boron trichloride, boron trifluoride and pyridinium hydrochloride, are not economically attractive for this use. Thus aluminium trichloride is preferred as the demethylating agent.

The process of the invention is preferably carried out using at least 0.33 mole of aluminium chloride per mole of trichloroanisole. The use of amounts of aluminium chloride less than the indicated one third mole per mole of trichloroanisole results in incomplete demethylation. It has also been found that xylene undergoes slight self-condensation (approximately 4.3% by weight) under the reaction conditions employed, thus consuming a fraction of the aluminium trichloride. Hence, to achieve maximum demethylation of trichloroanisole in practice, an excess (approximately 16% by weight) of aluminium trichloride above the one third mole per mole of trichloroanisole should be used.

The process of the invention is carried out at temperatures ranging from about 25° C. to the reflux temperature of the solvent used. The rate of demethylation is temperature dependent and the determination of reaction rate profiles at various temperatures has shown that at 50° C. the reaction is half completed in twelve and one half hours, whereas at 145° C. the reaction is essentially complete in three hours. The preferred temperature range for the demethylation reaction is 80° C. to 145° C.

In a preferred embodiment of the present invention, 1,2,4,5-tetrachlorobenzene is hydrolysed using conventional procedures, i.e. using methanolic sodium hydroxide, for a time period short enough so that the yield of 2,4,5-trichloroanisole is maximized and the formation of trichlorophenol and TCDD is minimized. The trichloroanisole, any unhydrolysed tetrachlorobenzene present and TCDD are then extracted from the alkaline aqueous sodium trichlorophenate solution by any of the water-immiscible organic solvents referred to above, but preferably xylene. The solution containing the trichloroanisole, tetrachlorobenzene and TCDD is dried by distillation to remove any water present, and is then treated with aluminium trichloride as set forth herein above.

Since the initial reaction on addition of aluminium trichloride to xylene solutions of trichloroanisole is vigorous at high temperatures, the aluminium trichloride should be added over an extended period or added at ambient temperature and the reaction mass then heated to the higher temperature.

After the demethylation is completed, the aluminium complexes are decomposed by treatment of the reaction product with water, the trichlorophenol formed is extracted with aqueous alkali. This alkali trichlorophenate solution may be added to that formed in the initial tetrachlorobenzene hydrolysis.

The xylene solution of tetrachlorobenzene and TCDD remaining is concentrated by xylene distillation and the residues returned to subsequent tetrachlorobenzene hydrolyses.

2,4,5-Trichlorophenol may be isolated from the alkali trichlorophenate solution in known manner. However, 2,4,5-trichlorophenol need not be isolated for its most usual use in the manufacture of 2,4,5-trichlorophenoxyacetic acid, but may be advantageously utilized as an aqueous solution of sodium 2,4,5-trichlorophenate.

The following experimental procedures demonstrate, with reference to FIGS. I to IV of the accompanying drawings, the optimum conditions for aluminium trichloride-trichloroanisole demethylation:

Experiment A: Quantity of Aluminium Trichloride

Three portions of trichloroanisole (each 0.1 gram (g) mole) in xylene (80 milliliter (ml)) were treated with aluminium trichloride (0.033, 0.022 and 0.011 g mole respectively) at 80° C. for five hours. A plot (FIG. I) of trichlorophenol yields versus aluminium trichloride used, shows that at least 0.33 moles of aluminium trichloride per mole of trichloroanisole are required to achieve near quantitive demethylation. The trichlorophenol was isolated as described in Example I below.

Treatment of xylene with aluminium trichloride under the above demethylation conditions resulted in formation of 4.3% of non-volatile product (based on initial weight of xylene). Thus an increase in the aluminium trichloride added for a demethylation reaction should be made to compensate for that consumed in this xylene self condensation in order to achieve maximum trichloroanisole demethylation. Assuming the self condensation product arises from two molecules of xylene, the increase should be 16% of the aluminium chloride charge.

Experiment B: Temperature of Demethylation

Reaction profiles (FIGS. II, III & IV) were determined for demethylations using the same quantities of materials (0.1 g mole trichloroanisole and 0.033 g mole aluminium chloride) as in Experiment A at 50°, 110° and 145° C. Trichloroanisole and trichlorophenol concentrations were determined on aliquots of reaction mass taken at intervals, after treatment with water and extraction with diethylether, by gas chromatography. The results show that the reaction proceeds at lower temperatures but to achieve a practical rate of demethylation the preferred, but not limiting, temperature range is 80° to 145° C.

Experiment C: Use of Alternative Solvents

Demethylations carried out at 80° C. for five hours in petroleum ether (boiling point (b.p.) 100°-120° C.), chlorobenzene and 1,2-dichloroethane, representative of the aliphatic, chloroaromatic and chloroaliphatic classes of solvents, gave 2,4,5-trichlorophenol yields (based on initial trichloroanisole) of 24, 24 and 66.7% respectively. Hence, although other solvents may be used for the demethylation, xylene is the preferred solvent.

Experiment D: Demethylation in Presence of Tetrachlorobenzene

A mixture of trichloroanisole (0.1 g mol; 21.15 g) and 1,2,4,5-tetrachlorobenzene (10 g) in xylene (80 ml) was heated at 80° C. with aluminium trichloride (0.05 mole; 6.65 g) for five hours. Trichlorophenol was isolated in 97% yield (based on trichloroanisole) as described in Example I below. Unchanged tetrachlorobenzene, together with xylene self condensation product (total 13.25 g) was isolated from the neutral product fraction after solvent removal.

The following examples further illustrate the present invention.

EXAMPLE I

A solution of trichloroanisole (21.15 g; 0.1 mole) in xylene (80 ml) was treated with aluminium trichloride (4.44 g; 0.03 mole) and agitated for five hours at 80° C. in a 250 ml 3-necked flask. Hydrochloric acid vapours evolved, were absorbed in a trap, containing water, connected to an outlet of the flask via a reflux condenser.

The resultant reaction mass was poured into ice-water (200 g), the lower aqueous layer separated and extracted twice with two further portions (50 ml) of xylene.

The combined xylene solution and extracts were washed with three portions (20 ml) of water and then extracted with aqueous sodium hydroxide (4 g sodium hydroxide in 100 ml water) followed by two further extractions (0.5 g sodium hydroxide in 50 ml water).

The combined alkaline extracts were acidified with concentrated hydrochloric acid (14 ml) to pH 1 and extracted four times with diethylether (50 ml).

The combined ether extracts were dried (anhydrous sodium sulphate), filtered and evaporated finally in vacuo to yield 2,4,5-trichlorophenol m.p. 66.5°–67.5° C.; literature m.p. 68° C. Equivalent weight was determined by potentiometric titration with alkali as 197.8, the theoretical value being 197.5. The product was an identical retention time on examination by gas chromatography with authentic 2,4,5-trichlorophenol. The yield was 17.54 g; 89% based on initial trichloroanisole. The 2,3,7,8-tetrachlorodibenzo-p-dioxin content, determined by gas chromatography after extensive column chromatographic clean up, was less than 2 ppb.

EXAMPLE II

In this preparation, all reactions and phase separation involved in washings and extractions, were performed in a series of 2 liter (l) 3-necked, mechanically agitated glass reactors, fitted with bottom stopcocks to enable inter-reactor gravity transfers of the various phases.

Trichloroanisole (211.5 g; 1.0 mole) was dissolved in xylene (350 g) and the solution dried by azeotropic distillation. The solution was treated with aluminium chloride (51.8 g; 0.39 mole) at 25° C. and then agitated at 110° C. for five hours.

After cooling to 85° C. the reaction mass was run, during ten minutes, into water (350 g) with agitation, the temperature rising from 25° C. to 56° C. The lower aqueous phase was separated and the organic phase washed twice with water (100 g) the aqueous phases then being uppermost.

The organic phase was then extracted with aqueous sodium hydroxide (40 g sodium hydroxide in 200 g water) by agitation for fifteen minutes at 45° C. Two further washings with water (200 g) were combined with the initial extract, giving the final sodium 2,4,5-trichlorophenate solution (842 g). 2,4,5-Trichlorophenol concentration, determined bromometrically, was 22.6% by weight, corresponding to a 96.4% yield, based on initial trichloroanisole. The 2,3,7,8-tetrachlorodibenzo-p-dioxin content, determined by gas chromatography, after extensive column chromatographic clean up, was less than 2 ppb.

What we claim is:

1. A process for the production of 2,4,5-trichlorophenol containing very low concentrations of the impurity 2,3,7,8-tetrachlorodibenzo-p-dioxin, which comprises demethylation of 2,4,5-trichloroanisole, by treatment of said 2,4,5-trichloroanisole with aluminium chloride at temperatures of from about 25° C. to reflux temperature of the reaction mixture in an aromatic, chloroaromatic, aliphatic or chloroaliphatic hydrocarbon solvent.

2. A process as claimed in claim 1, in which the aluminium chloride is used at the rate of at least 0.33 mole per mole of trichloroanisole.

3. A process as claimed in claim 2, in which the solvent is xylene.

4. A process as claimed in claim 3, in which the demethylation reaction temperature range is from 25° C. to 145° C.

5. A process as claimed in claim 4, in which the demethylation reaction temperature range is from 80° C. to 145° C.

* * * * *